(12) United States Patent
Kaye-Wilson

(10) Patent No.: US 7,284,863 B2
(45) Date of Patent: Oct. 23, 2007

(54) DEVICE AND METHOD FOR VIEWING OCULAR MEDIA

(75) Inventor: Lo Kaye-Wilson, Wales (GB)

(73) Assignee: Zygomatics, Ltd., Garelochhead (GB)

( * ) Notice: Subject to any disclaimer, the term of this patent is extended or adjusted under 35 U.S.C. 154(b) by 524 days.

(21) Appl. No.: 10/362,042

(22) PCT Filed: Aug. 23, 2001

(86) PCT No.: PCT/GB01/03785

§ 371 (c)(1),
(2), (4) Date: Jul. 28, 2003

(87) PCT Pub. No.: WO02/15773

PCT Pub. Date: Feb. 28, 2002

(65) Prior Publication Data

US 2004/0012759 A1    Jan. 22, 2004

(30) Foreign Application Priority Data

Aug. 23, 2000 (GB) ................................. 0020728.2

(51) Int. Cl.
*A61B 3/10* (2006.01)
(52) U.S. Cl. ................... 351/218; 351/200; 351/205
(58) Field of Classification Search ............... 351/200, 351/205, 211, 221, 246, 216–218
See application file for complete search history.

(56) References Cited

U.S. PATENT DOCUMENTS

| | | | | |
|---|---|---|---|---|
| 2,135,743 A | | 11/1938 | Cassity | 351/205 |
| 2,367,855 A | * | 1/1945 | Ettinger | 351/211 |
| 2,501,438 A | * | 3/1950 | Copeland | 351/211 |
| 3,441,340 A | * | 4/1969 | Connors et al. | 351/221 |
| 3,466,122 A | * | 9/1969 | Ben-Tovim | 351/211 |
| 3,572,910 A | * | 3/1971 | Koester | 351/211 |
| 3,583,795 A | * | 6/1971 | Heine | 351/221 |
| 3,586,424 A | | 6/1971 | Schenk et al. | 351/213 |
| 3,861,789 A | * | 1/1975 | Heine | 351/218 |
| 4,220,401 A | * | 9/1980 | Muchel | 351/211 |
| 4,552,440 A | | 11/1985 | Guyton | 351/214 |
| 4,682,867 A | | 7/1987 | Gould | 351/223 |
| 4,902,124 A | | 2/1990 | Roy, Sr. et al. | 351/223 |
| 4,993,827 A | | 2/1991 | Benedek et al. | 351/221 |

FOREIGN PATENT DOCUMENTS

DE      8704606 U     7/1988

* cited by examiner

*Primary Examiner*—Huy Mai
(74) *Attorney, Agent, or Firm*—RatnerPrestia

(57) ABSTRACT

An ophthalmic device for the examination and detection of opacities in the ocular media comprising a cylindrical housing, a reflecting means located in the housing adapted to reflect light through an illuminating through-hole in the housing, and a viewing port in the housing disposed opposite the illuminating through-hole, the illuminating through-hole, the reflecting means and the viewing port being adapted to define a light path.

26 Claims, 11 Drawing Sheets

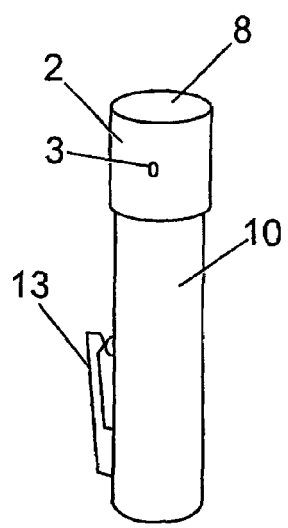 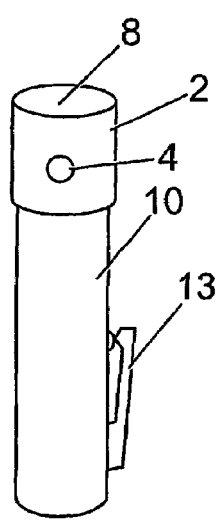 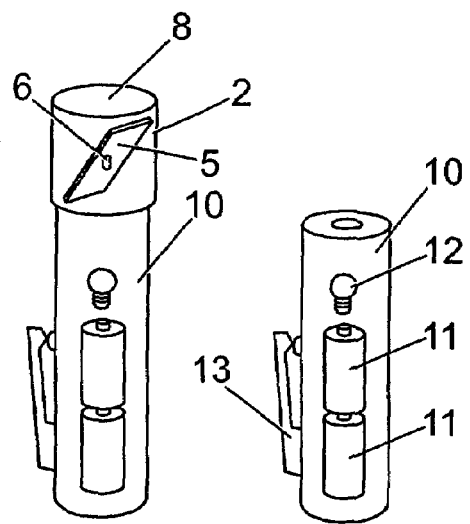
Fig. 4    Fig. 5    Fig. 6a    Fig. 6b
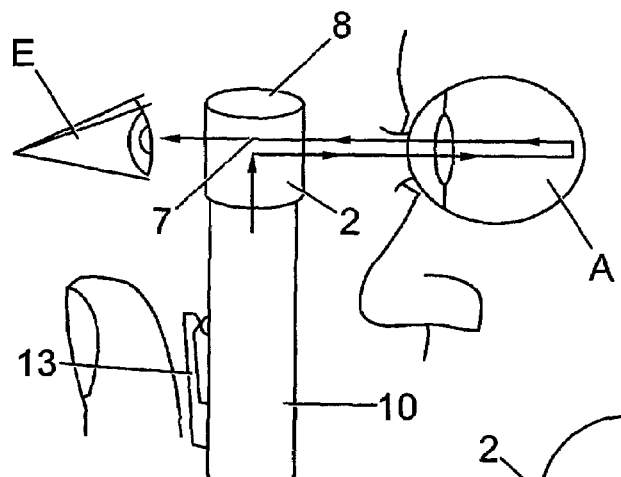
Fig. 7
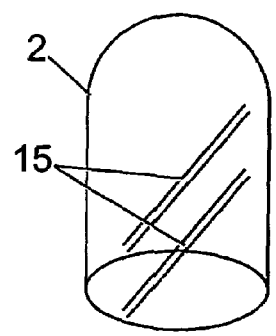 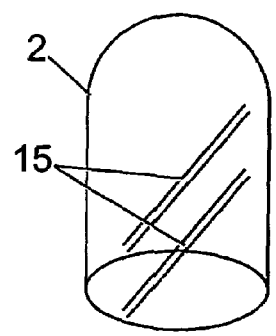
Fig. 9    Fig. 8

DEVICE AND METHOD FOR VIEWING OCULAR MEDIA

The present invention relates to an ophthalmic device for detecting opacities in the ocular media including detecting and quantifying cataract.

In general the final filter for all ophthalmic referrals is non specialist medical doctors. Opticians can refer patients to the hospital eye services, but at the present time, all referrals are generally screened by doctors before onward referral to an Ophthalmologist. For cataract referrals it would be helpful to know whether reduced acuity is due to cataract or due to some other cause. It would also be helpful to use a simple test which would identify cataract and allow some apportioning of blame for reduced acuity. This would also make very apparent when cataract is not the cause of the problem, at which point the doctor should consider other causes of visual loss, for example vascular occlusion, macular degeneration or retinal detachment. This is a clinically significant problem because all of the above examples of causes of visual loss may actually benefit from prompt medical intervention. As medical intervention may be less effective at a later stage, there are often medicolegal implications for conditions which have been missed, having been wrongly diagnosed as cataract.

Finding or referring appropriate cases for cataract surgery is a very major problem in Third World countries, for example, where surgical resources are very limited, often serving very large populations in rural areas. It has been suggested, when analysing the dynamics of Third World high volume "Cataract Camps" that the major problem with these endeavours is not the surgery itself but actually finding enough patients to be operated on when the mobile "Camp" visits an area. Exactly the same difficulty applies to non-mobile cataract services; resources for surgery are usually centralised and therefore quite inaccessible to the majority of people. As prospective patients may need to travel great distances, it is vital first to go out into the community in order to find those patients who will benefit from cataract surgery. However, as the workers who examine these patients in the distant communities are often not medically trained, a simple way of identifying cataract would be very helpful.

An object of the invention is to overcome the problems of the prior art.

An ophthalmic device comprising a housing, reflecting means in the housing adapted to reflect light through an illuminating through-hole in the housing, a viewing port in the housing disposed opposite the illuminating through-hole, the illuminating through-hole, the reflecting means and the viewing port being adapted to detect ocular opacities in the absence of a retinal image forming capacity.

Preferably, the illuminating through-hole, the reflecting means and the viewing port are adapted to define a co-axial light path.

Preferably, the device is adapted to receive a light source. Alternatively, the device comprises an integral light source.

Preferably, the light source is homogenous, thus enhancing the positive assessment of visual acuities under investigation.

Typically, the reflecting means has a generally planar reflecting surface orientable at an angle to maximise the reflection of light through the illuminating through-hole. Preferably, the reflecting surface is orientable at an angle of approximately 45° to the light source.

Advantageously, the reflecting means comprises a one-way see-through mirror. Alternatively, the reflecting means comprises a standard mirror having a reflecting means through-hole, such that the illuminating and reflecting means through-holes and the viewing port define the light path.

Preferably, the reflecting means comprises a prismatic shaped reflecting means having a reflecting means through-hole, such that the illuminating and reflecting means through-holes and the viewing port define the light path.

Typically, the housing comprises a cylindrical tube and can be made of any suitable material, for example, plastics.

Preferably, the cylindrical tube comprises a reflecting means mounting. Suitably, the reflecting means mounting comprises a pair of grooves on the inner walls of the cylindrical tube for receiving the reflecting means.

Optionally, glue may be used on its own or in conjunction with the grooves to secure the reflecting means in position.

Preferably, the light source is a suitable monochromatic light source. Alternatively, the light source comprises a conventional light source.

Advantageously, the light source comprises a pen torch receivable by an open end of the cylinder such that the light emittable from the pen torch falls on the mirror. Alternatively, the light source comprises a light emitting diode (LED), preferably a LED emitting red light.

Preferably, the inner walls of the cylinder comprises a stop means intermediate one end of the cylinder and the mirror to limit the depth of insertion of the light source into the cylinder.

Preferably, an end of the cylinder remote from the light source is closed. The remote end of cylinder may be sealed by, for example, a plastic cap. This helps prevent light other than from the light source entering the device and also reduces dirt ingress. It also provides added structural rigidity to the device and prevents the reflecting means from twisting especially when the cylinder portion is made of a less rigid material.

According to a further aspect of the invention, there is provided an ophthalmic device comprising a housing, prismatic shaped reflecting means in the housing adapted to reflect light through an illuminating through-hole in the housing, a viewing port in the housing disposed opposite the illuminating through-hole, the illuminating through-hole, the reflecting means and the viewing port being adapted to detect ocular opacities in the absence of a retinal image forming capacity.

According to a further aspect of the invention, there is provided an ophthalmic device comprising a housing, a light source adapted to direct light along a first light path through an an observation port in the housing, and a view port in the housing disposed opposite the observation port, the light source, the observation port and view port being adapted to detect ocular opacities in the absence of a retinal image forming capacity.

Preferably, the observation port and view port define a second light path.

Preferably, the first and second light paths form an angle of less than 10°.

Preferably, the first and second light paths form an angle of between 5° and 10°.

According to a further aspect of the invention, there is provided a method for the detection and examination of visual acuities and opacities in the ocular media comprising the steps of directing light into an eye of a patient, allowing at least a portion of the light to be reflected from the eye of the patient and observing the light reflected from the eye along the same light path as the majority of the reflected light emerging from the eye.

The light reflected from the eye is observed along a light path which forms an angle of less than 10° with the light directed into the eye of the patient.

Preferably, the light reflected from the eye is observed along a light path which forms an angle of between 5° and 10° with the light directed into the eye of the patient.

More preferably, the patient's eye, the light reflected from the patient's eye and the observer's eye define a single light path.

The present invention employs a retroillumination technique. The invention provides an effective and simple method suitable for use by non-ophthalmologists.

When a light is shone into the eye, some of the light shines back from out of the eye. This is most clearly seen in the feline or canine eye. The animal retina reflects back a large amount of diverging light at the observer, allowing the reflection to be seen over quite a large angle. In the human eye, the reflected light exits the eye in a less divergent state than from the animal eye. For this reason, in order to see the reflected light, one has to be observing the human eye along the same light pathway as the majority of reflected light emerging from the eye. Ideally then, one would need to be looking along the rays of the illuminating light which would be both incident and reflected along the same pathway. The observer's eye and the point source of illuminating light would ideally be at exactly the same place. This is called coaxial illumination. This phenomenon explains why subjects in flash photographs often have red pupils. The light from the flash gun is reflected from the back of the eye and captured on camera as the lens aperture of the camera is usually very close to the point source of the flashlight. The rich choroidal blood vessel circulation in the wall of the eye provides the characteristic red colour.

The ophthalmic device of the present invention supplies coaxial illumination to detect opacities in the ocular media and is adapted to provide field workers throughout the world with an appropriate instrument for detecting and even quantifying cataract. The device identifies those cases most likely to benefit from cataract surgery. The ophthalmic device of the present invention exploits the coaxial illumination principle on which the ophthalmoscope is based. The ophthalmic device produces an image of the patient's lens visible to the observer for the assessment of the patient's eye. It is preferable that the device should be used in a darkened room so that the patient's eyes may adapt without the need to resort to mydriatic drugs. The light emitted from the light source can be any visible light which will result in the easy viewing of the lens of the patient by the observer. The image of the lens of the patient and the visual acuity, for example, a cataract, are easy to obtain and are not dependent to any significant degree on the precise alignment of the ophthalmic device. Images of the lens produced are of a good quality for eyes requiring up to plus/minus 5 diopters of correction. Use outside these limits would be good but not essential. The patient's pupil can be assumed to be between 4-5 millimetres in diameter and in practice is likely to be larger. The ophthalmic device will not produce a numerical value for the visual acuity assessment and training for use of the ophthalmic device may include an instruction sheet with photographs indicating the various forms of visual acuity such as cataract formation. Detection of visual acuities may also be improved by assessing the cornea and by an unaided visual examination before using the ophthalmic device.

The device can be made in a simple clip-on form to be used in conjunction with a readily available battery-operated pentorch and may improve case finding globally, advancing the World Health Organisation's VISION 2020 aims of eradication of all avoidable blindness by the year 2020.

One of the chief uses of an ophthalmoscope today is the provision of a red reflex by coaxial illumination in order to detect opacities in the media. The global problem for case finding in ophthalmology is enormous and the task of providing ophthalmoscopes and the necessary training in the use of ophthalmoscopes to all field workers throughout the world would be even more onerous. The ophthalmoscope is really the best way of retroilluminating cataracts, often giving a better impression of degree of cataract than the slit lamp binocular microscope used by ophthalmologists in clinics. However, as indicated previously, because of the need to adjust the settings on an ophthalmoscope, non-ophthalmologists often find it difficult to achieve retroillumination with known ophthalmoscopes. The present invention removes the need for adjustment, as the device has no moveable settings.

A simple way of identifying people who need ophthalmological assistance is to train field workers to check visual acuity. Onward referral can be arranged for those with vision below a certain level. This is however a very non-specific way of testing for cataract. A large proportion do not have cataract, and such an approach do not feed patients efficiently into a high volume cataract service.

Eye checks for all people above a certain age either by local health professionals or at a central unit would be an ideal approach. However, in many countries, numbers of people to be examined and the absence of local health professionals mean that the only way to screen for cataract is in the field, using the rather crude method of checking visual acuity. To some extent this is true in the developed world also; accurate G.P. and optometrist screening would allow more effective referrals of patients, especially with the possibility of referral into the fast-track cataract units which are now being established.

The invention will now be described by way of example only with reference to the accompanying drawings in which:—

FIG. 4 is a perspective rear view of the ophthalmic device mounted on a pen torch;

FIG. 5 is a front view of FIG. 4;

FIG. 6(a) is a view similar to FIG. 4 with hidden internal hidden detail showing the light source of the pen torch and mirror of the ophthalmic device;

FIG. 6(b) shows the pen torch of FIG. 6(a) separated from the ophthalmic device;

FIG. 7 shows a schematic diagram of the ophthalmic device together with pen torch in use;

FIG. 8 is a perspective view from below of an alternative embodiment of the ophthalmic device having a different shaped housing;

FIG. 9 is the ophthalmic device of FIG. 8 with hidden internal detail showing grooves on the internal walls of the housing for receiving and holding in place the mirror of the ophthalmic device;

Figure 1:
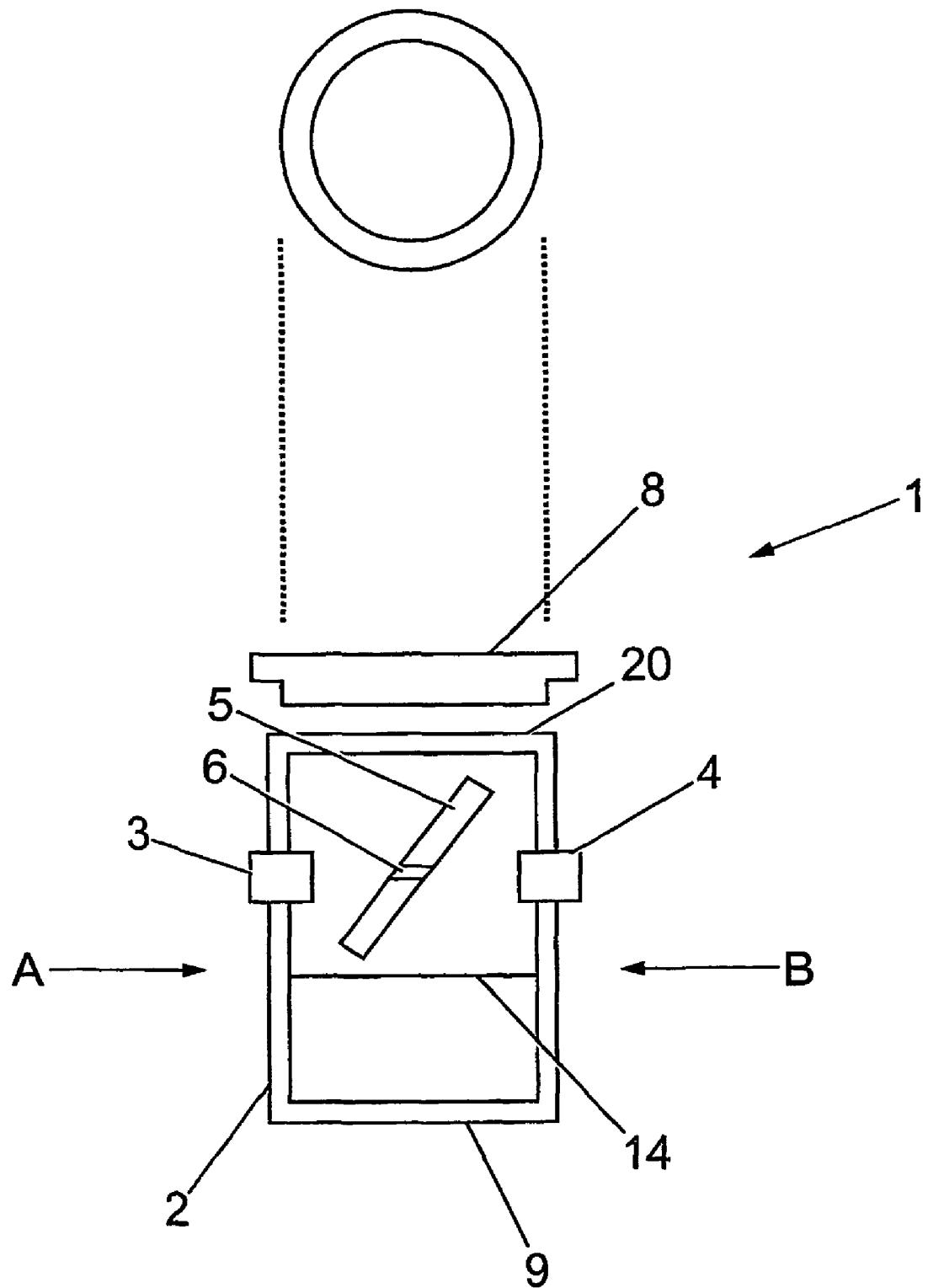
FIG. 1 is a cross sectional and partially exploded view of the ophthalmic device according to the present invention.
Figure 2A:
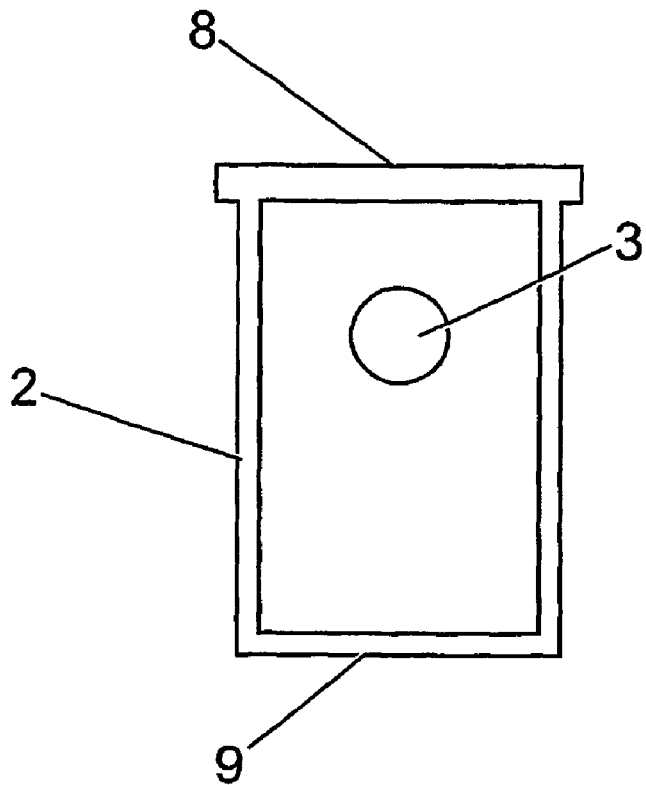
FIG. 2(a) is a view, in the direction of arrow A in FIG. 1, of the ophthalmic device.
Figure 2B:
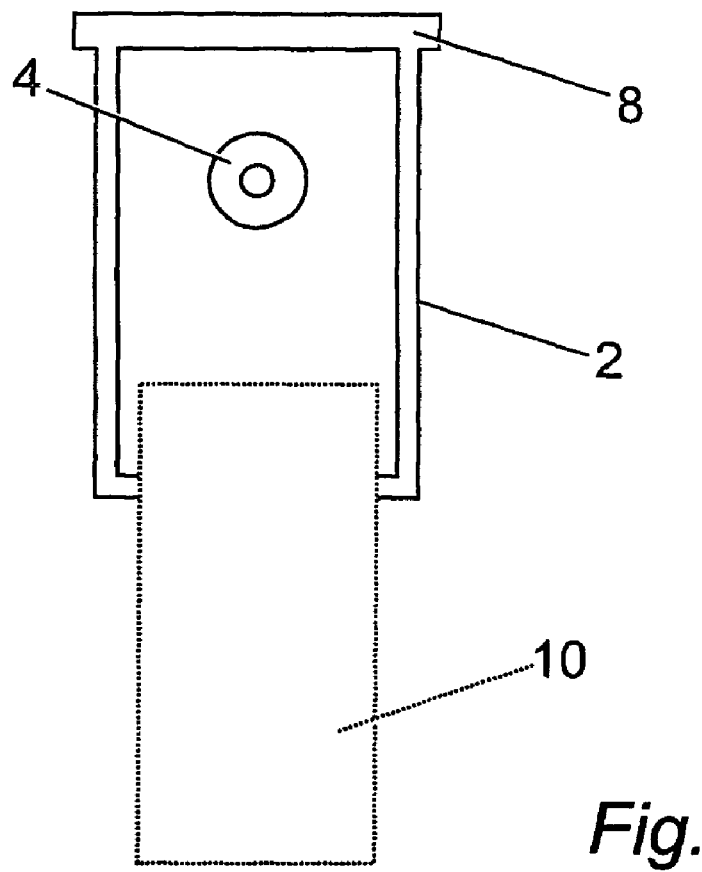
FIG. 2(b) is a view, in the direction of arrow B in FIG. 1, of the ophthalmic device, shown here mounted on a pen torch.
Figure 3:
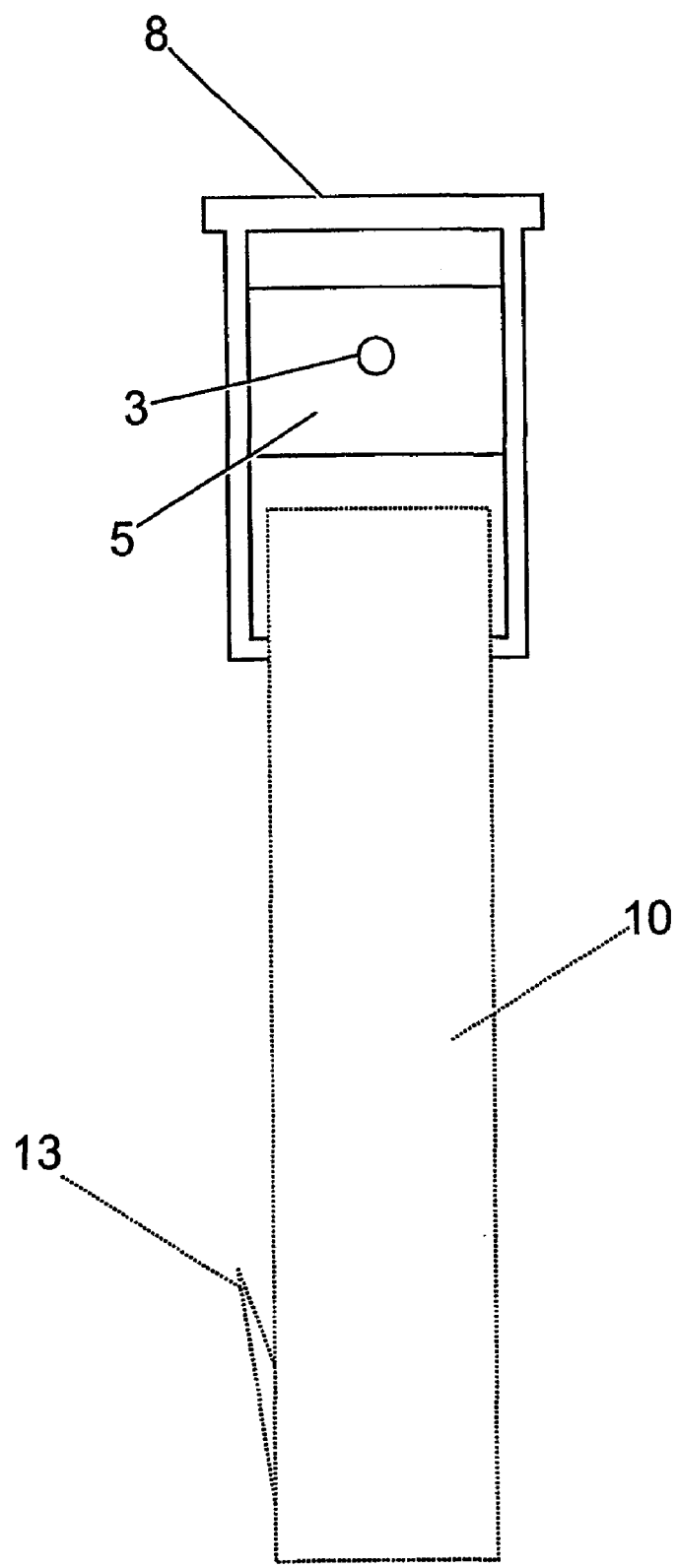
FIG. 3 is a view similar to FIG. 2(a) with hidden internal detail showing the mirror, and the ophthalmic device being mounted on a pen torch.

Referring to the drawings, there is shown an ophthalmic device according to the present invention, indicated generally by the reference numeral 1, comprising a cylindrical housing 2 having a viewing port 3 generally midway along the cylindrically shaped wall of the housing 2 and an illuminating port 4 positioned opposite the viewing port 3. A mirror 5 having an aperture 6 at its centre is positioned intermediate the ports 3 and 4 such that the centres of the ports 3, 4 and the aperture 6 are co-axial and define a light path 7.

A sealing cap 8 closes one end 20 of the housing 2. An open end 9 of the housing 2 receives a pen torch 10. The pen torch 10 comprises standard batteries 11, light bulb 12 and handle 13. Stop means 14 in the form of a groove extending the internal circumference of the housing 2, and intermediate the open end 9 and the mirror 5, limits the insertion of the pen torch 10 into the housing 2. Retaining grooves 15 on the internal walls of the housing 2 receive and hold the mirror 5 so that its reflecting surface lies at an angle of 45° to the torch 10. The cap 8 keeps light from above out of the device 1 and also reduces the amount of dirt ingress. The cap 8 also provides added structural rigidity to the walls of the housing 2. This protects the mirror 5 from twisting.

In use, the illuminating port 4 is placed adjacent a patient's eye A so that, as near as possible, the observers eye E, the ports 3, 4 and the patient's eye A are co-axial. This can be seen most clearly in FIG. 7. The light from the pen torch 10 is deflected by the mirror 5 through the port 4 and illuminates the retina of the eye. The illuminated retina can then be observed along the light path 7 defined by the ports 3, 4 and aperture 6, allowing for detection of developing cataract, opacities and reduced acuity.

During examination of the patient's eye the observer may contact the patient to steady the device, for example, by placing a hand on the patient's forehead. While no contact is made with the eye of the patient the observer may hold the lid of the eye in an open position. The patient can be in any position, from standing to supine during examination.

Figure 10:
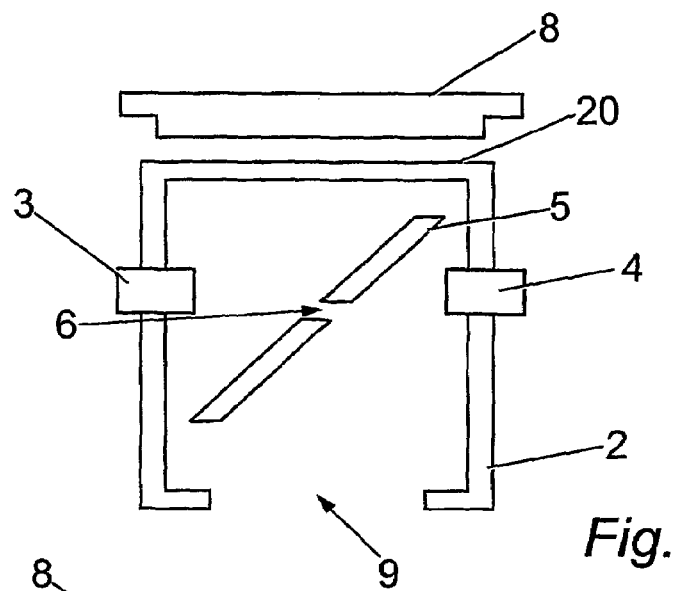
FIG. 10 is the ophthalmic device of FIG. 1 clearly showing the aperture in the mirror.
Figure 11:
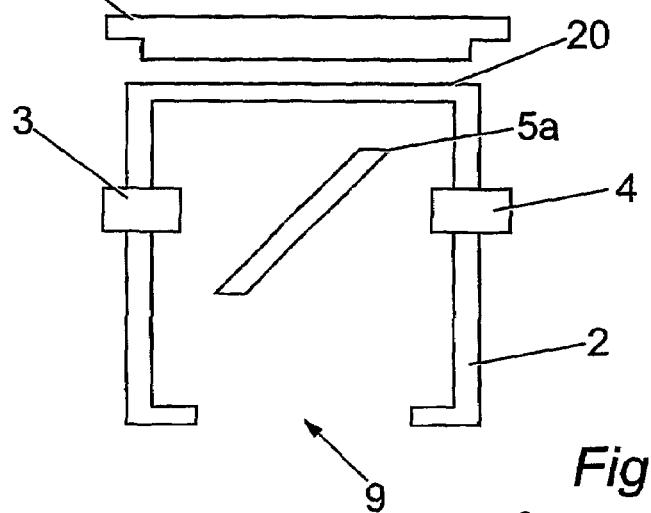
FIG. 11 is the ophthalmic device of FIG. 1 showing a "one-way see-through" mirror without an aperture.
Figure 12:
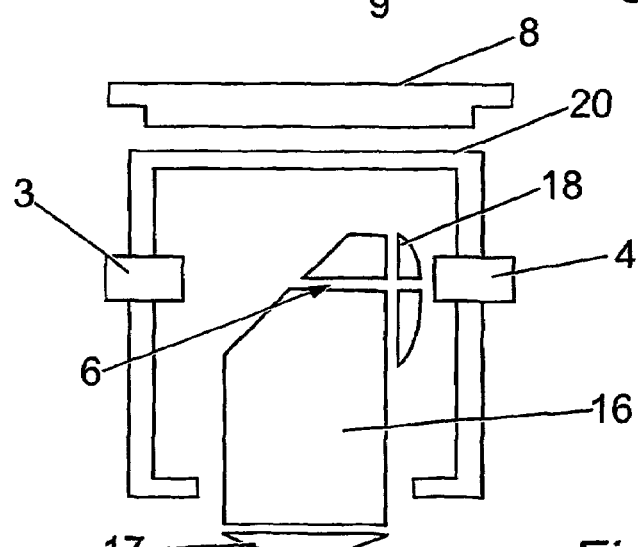
FIG. 12 is the ophthalmic device of FIG. 1 having lenses and a prismatic shaped light reflector with an aperture through the reflector and one of the lenses.

FIG. 10 is a further view of the ophthalmic device clearly showing the aperture 6. FIG. 11 and FIG. 12 show a "one-way see-through" mirror 5a and a prismatic shaped light reflector 16 with lenses 17 and 18 respectively. The "one-way see through" mirror 5a or the prismatic shaped light reflector 16 may include an aperture 6 therein as appropriate.

Figure 13:
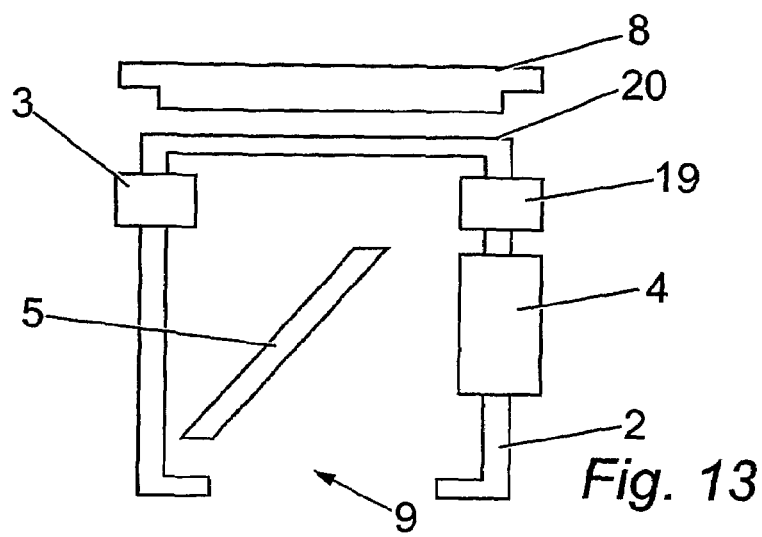
FIG. 13 is an alternative embodiment of ophthalmic device having a larger illuminating port and additional observation port.
Figure 14:
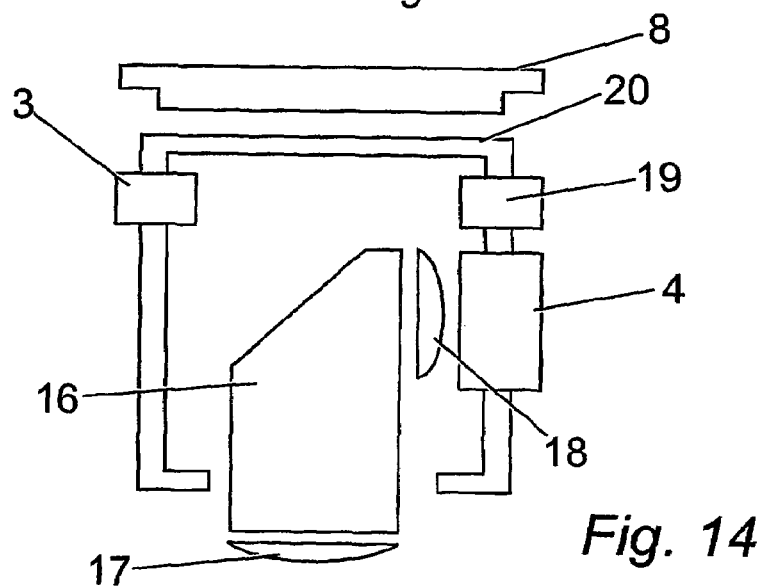
FIG. 14 is the ophthalmic device of FIG. 13 having lenses and a prismatic shaped light reflector.
Figure 15:
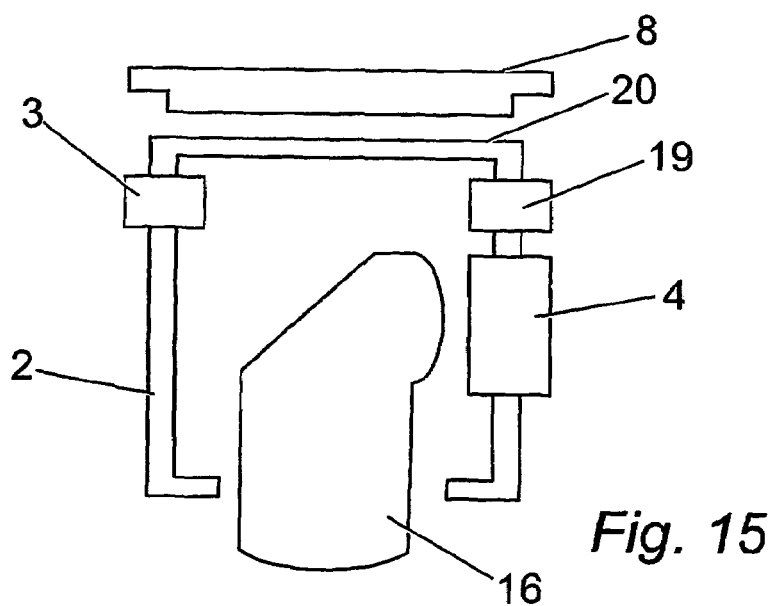
FIG. 15 is the ophthalmic device of FIG. 14 wherein the lenses form an integral part of the light reflector.

FIG. 13 to FIG. 15 are views of a further alternative embodiment of the invention wherein the housing has a larger illuminating port 4 and an observing port 19 wherein the "one way see-through" mirror 5a and illuminating port 4 define a first light path and the viewing port 3 and observing port 19 define a second light path. This embodiment allows the retina to be viewed at a different angle.

Although the applicants do not wish to be bound by any particular embodiment or use of the ophthalmic device, in order to understand the invention more clearly a general description will now be given in relation to the design, evaluation and use of the ophthalmic device and in particular its use in relation to diagnosing and monitoring cataract development.

As a first step in the design of the ophthalmic device 1, a number of suitable optical parameters were chosen. Using these parameters, two computer based simulations were run. The majority of the work was undertaken using Opticad 6.02 (Focus Software, Tucson, USA). This package is based upon non-sequential ray tracing. In addition levels of scattering can be included into the optical parameters and this is used to simulate different levels of cataract formation once the overall design of the instrument has been determined. Optimisation of the ophthalmic device 1 is undertaken using Beam 4 (Stellar Software, Berkley, USA), an optical design package including diffraction effects.

The eye model in both software packages is based upon one used for the design and development of an ophthalmic laser system and ophthalmic contact lenses. It includes three layers for the cornea and the lens is divided into a crystalline and nuclear section. The aspheric optical properties of the lens and cornea are also included.

In the Opticad model the retina is assumed to be a reflector whose reflectance can be altered. The scattering induced by the cataract is assumed to be Lambertian in line with accepted ophthalmic properties of most cataracts. The birefringent nature of some cataracts is not included in the model.

The performance of the eye model is evaluated using two figures of merit produced by the software simulations. The total energy passing back through the ophthalmic device onto a "film" is recorded as the optics were manipulated. The energy distributions onto the final optical surface (screen or lens) and the eye's lens are examined. For a "normal" non-cataractus eye the returned distribution should be uniform and should be illuminating most of the eye's lens. As the scattering within the lens increases this should be reflected in the distribution on the final optical surface. The energy distribution from a normal eye was also used to investigate the tolerance of the ophthalmic device to miss-alignment. The energy distribution on the retina is also examined in order to develop an estimate for the effect of the light causing the iris within the eye to close.

Two options are considered for the light source. The first is to use a conventional bulb and the second option a LED based light source. In order to produce a bright, back illumination of the potential cataract a good reflection from the retina is required and the original concept of the ophthalmic device came from the examination of flash photographs with "red-eye". In order to maximise the reflection and minimise the light absorbed by the retina it was decided that the light source should be spectrally filtered to a band in the red portion of the optical spectrum (around 620 to 670 nm). This matches the point at which the reflectivity is at a peak and the absorption a minimum, but which an observer will still be able to visualise. Light in the yellow and green portion of the spectrum, although easier to see will not be reflected as well but more importantly will cause the patient's iris to close, thus limiting the field of view of the lens.

Conventional tungsten bulbs do emit the majority of their light in the red, particularly if run below their full operating voltage but they are typically only around 5% efficient in the conversion of electrical to optical energy. For a small 1 W torch bulb powered by two AA batteries the average life expectancy is anticipated to be around 1 hour of continual use. Of the 50 mW (maximum) optical output around 5% is useable red light. (This is after collection, collimaton and spectral filtering). This might just be sufficient light to see through a moderately thick cataract. However, for efficient visualisation of well developed cataracts it is estimated that a bulb 5 times brighter is required. This would necessitate larger "C" sized batteries. In addition, such bulbs generate significant quantities of heat that would need to be removed and may lead to complications in the design of the housing 2. (Experience has shown that ophthalmic instruments using such light sources can easily have a housing temperature exceeding 50° C., which is above the permitted temperature for hand contact in medical instruments).

An alternative light source is a visible LED. Such devices operate very efficiently over the spectral region of interest and can be purchased with powers in excess of 30 mW in 5 mm diameter packages. Such an LED source would deliver sufficient light to the observer even through thick cataracts. With a power consumption of around 40 mA the lifetime of a pair AA batteries should be in excess of 6 hours continual operation.

Critical to the successful operation of the ophthalmic device having a LED as the light source is the efficient collection and manipulation of the light. Using a combination of lenses and apertures a homogenous patch can be achieved with a minimum of two lenses and an aperture. The lenses do not need to be of high optical quality, a plastic moulded optics would be sufficient.

It is decided, therefore, and for the purpose of this particular use that the ophthalmic device should employ a red LED.

Figure 16:
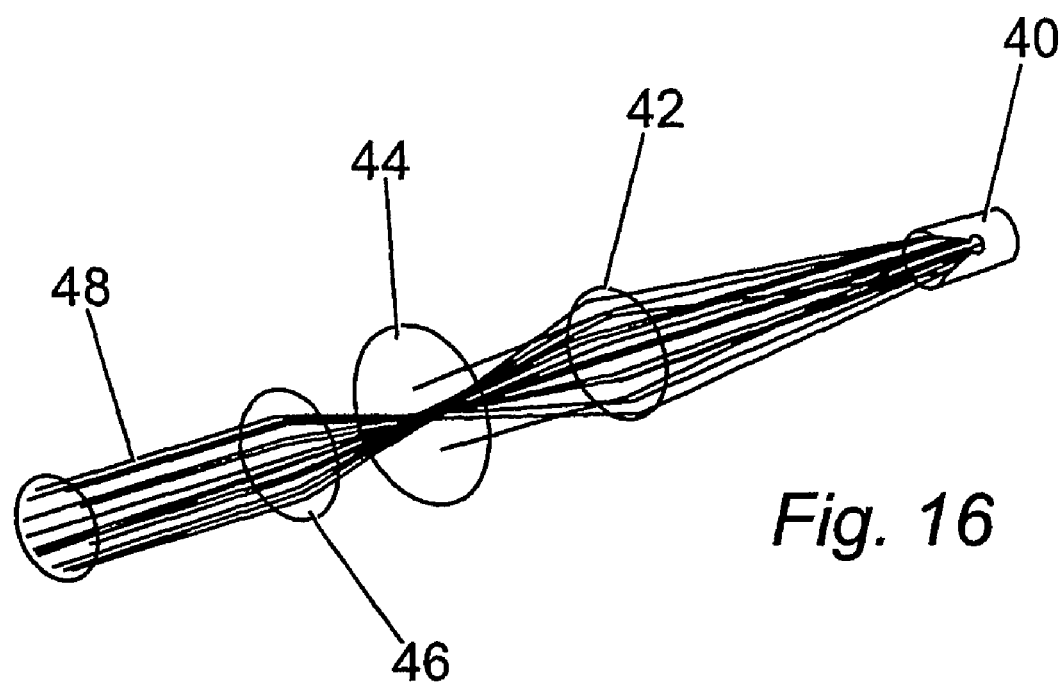
FIG. 16 shows an alternative arrangement of lenses and light source for use with the ophthalmic device.
Figure 17:
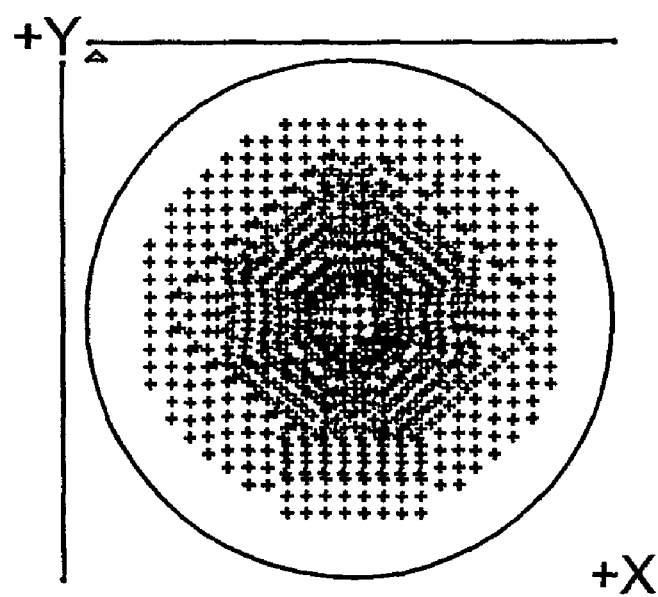
FIG. 17 shows a light intensity plot of the light beam obtained using the optical arrangement of lenses and light source of FIG. 16.

It was found, using the optical arrangements as shown in the schematic representation in FIG. 16 which comprises the red LED source 40, a collimation lens 42, an aperture 44 and an objective lens 46 that a homogenous light beam 48 could be produced suitable for use with the ophthalmic device of the invention to create a homogenous image. The Intensity variation across the beam 48 is around 15% within the region that can be expected to enter the eye. The light intensity plot of the beam 48 is shown in FIG. 17. The exact dimensions and placement of the collimation and objective lenses 42 and 46 can be altered within certain tolerances, which are determined by the working distance of the instrument. Typical figures for a 10 mm focal length collimation lens 42 give an optical length from the LED 40 to the objective lens 46 of 39 mm. The position of the objective lens 46 creates a homogenous beam 48 having the proper optical parameters for delivery into the eye E.

The delivery of the light to the eye E must fulfil several requirements. It should be as close to the optical axis of the eye E as possible in order to illuminate as much of the eye's lens as possible. The observation path should be close to the illumination axis for the same reason but reflections from the cornea should be as low as possible. Two options using the ophthalmic device of the invention are illustrated in FIGS. 18 and 19 and these options correspond to the two embodiments of the ophthalmic device as illustrated in FIGS. 10 to 12 and FIGS. 13 to 15 respectively.

Figure 18:
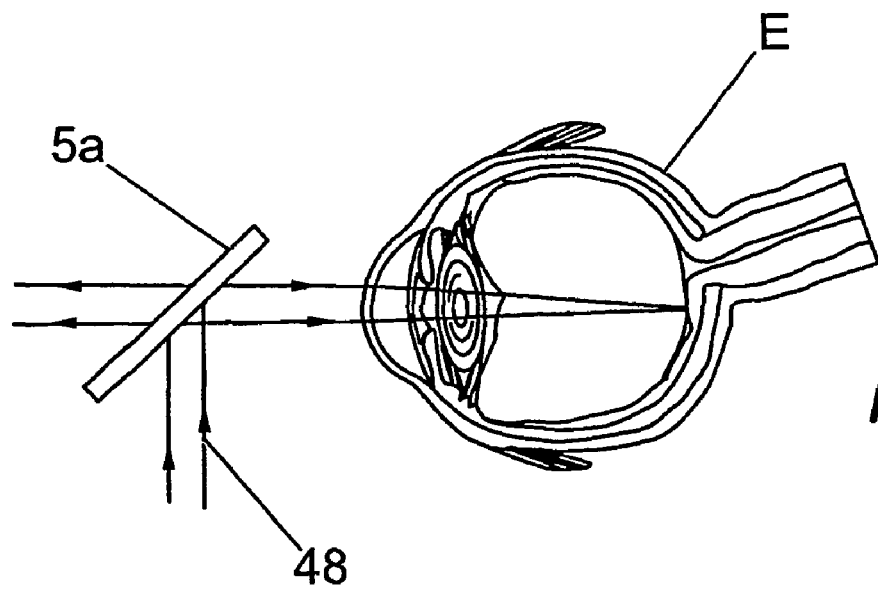
FIG. 18 shows a way of viewing the patient's eye using the embodiment of ophthalmic device shown in FIGS. 1 and 10 to 12.

As illustrated in FIG. 18 the light is sent into the eye E via a semi-silvered, one way see-through mirror 5a or a mirror 5 with a hole in the centre. The light reflected from the eye E is then viewed through the mirror by the observer. The advantage of this technique is that the alignment of the ophthalmic device is easier.

Figure 19:
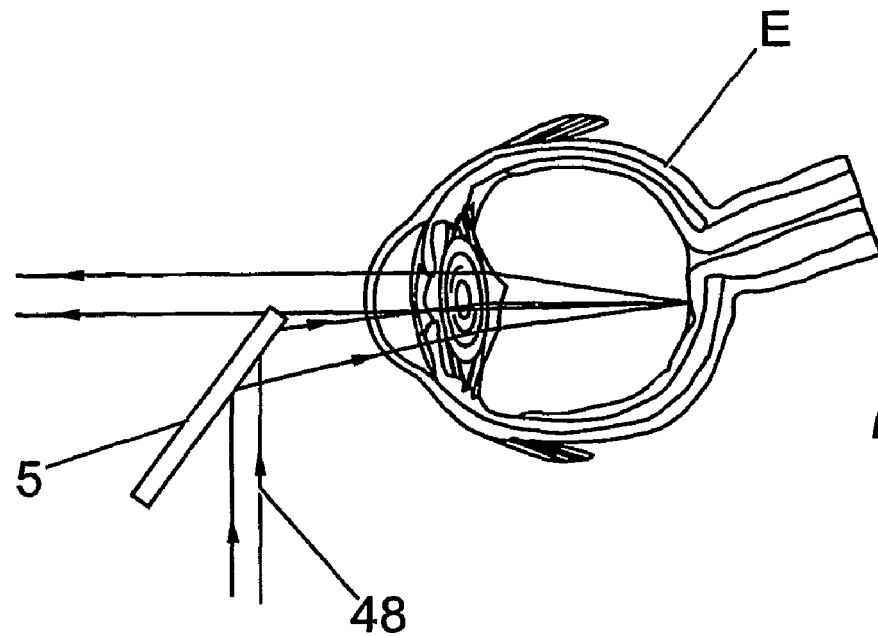
FIG. 19 shows a way of viewing the patient's eye using the embodiment of ophthalmic device shown in FIGS. 13 to 15, 20 and 21.

As illustrated in FIG. 19, the light reflected from the eye E is observed over the top of the mirror 5. In this case the mirror 5 can be a standard mirror. This ophthalmic device requires a greater degree of skill to operate and to acquire an image but the image obtainable is of a high quality. Care should be taken with the internal surfaces of the instrument to prevent stray reflections which would affect the quality of the image. This technique is also used by the more expensive ophthalmoscopes and is preferred option for the detection and examination of cataract development.

When using the ophthalmic device of FIG. 19 the two optical axes (i.e. of the light beam directed into the eye E and the light beam reflected therefrom) should preferably be as close together as possible in order to facilitate use of the ophthalmic device and obtain a good image.

Figure 20:
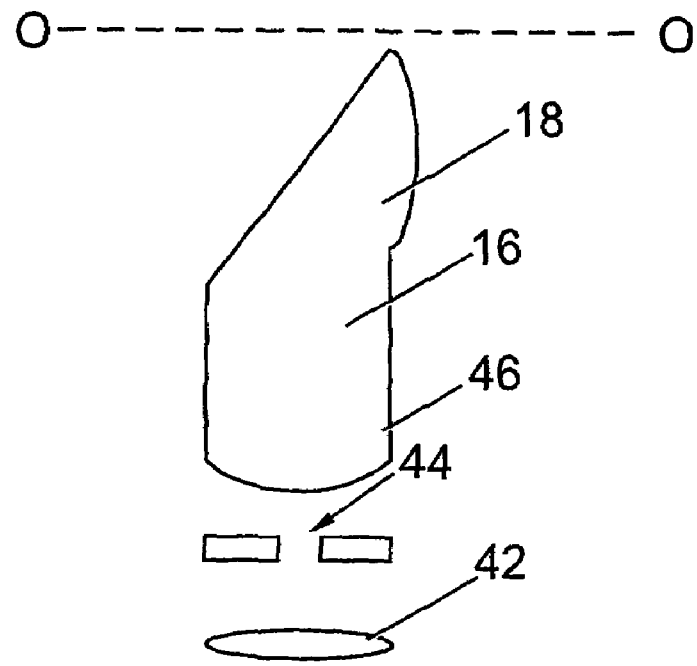
FIG. 20 is a schematic view of a further embodiment of ophthalmic device shown here without the housing.
Figure 20:
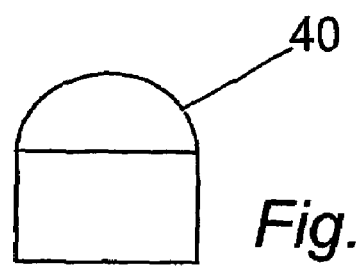

The LED 40 can be mounted in a "lolly-pop" style handle as shown in FIGS. 1 to 6 where the LED 40 replaces the conventional light bulb 12. The light may be reflected using the standard mirror 5 or by silvering the internal walls of the housing 2. The two lenses (17, 18) and (42,46), aperture (6, 44) and mirror 5 may be moulded as one component as shown in FIG. 20 or assembled from standard optical elements.

Figure 21:
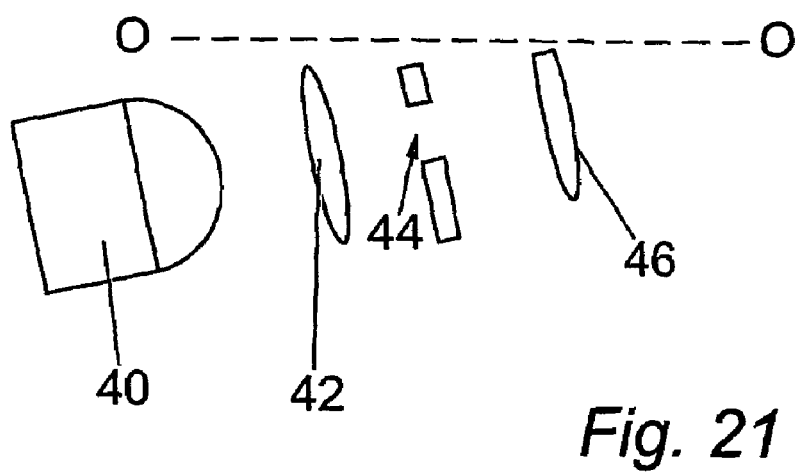
FIG. 21 is a schematic view of yet a further embodiment of ophthalmic device without the housing using near co-axial illumination without reflecting means.

An alternative approach is to mount the LED 40 and lenses (17, 18), (42, 46) close to the observer's optical axis O. This technique illustrated in FIG. 21 may remove the requirement for a mirror 5 but to place the LED 40 and lenses (17, 18), (42, 46) close to the optical axis the objective lens (48, 46) may require a "V" groove machined in top (not shown). This will aid the observer's initial alignment and also ensure a close optical axis for illumination and observation of the eye E. The arrangement of optical devices shown in FIG. 21 is known as a "camcorder" design. Both of the observation techniques illustrated in FIGS. 20 and 21 require less illumination than the technique employing the semi-silvered mirror 5a as shown in FIGS. 11 and 18.

There are a number of ways to observe the light reflected from the eye E. The reflected light may be viewed directly by the observer, where the eye of the observer is close to the ophthalmic device. This is the standard method used when operating ophthalmoscopes and has the benefit of flexibility and low cost. Certain refractive errors in the patient's eye E can be accounted for by the observer's natural accommodation. The optical axis O of the observer is not rigidly defined and a skilled operator would be able to move his head around and examine sections of the lens of the eye E which may be difficult to view. A disadvantage of this freedom of movement is that it may be harder initially to obtain an image and to ensure that the observations are made of the cataract. In addition, it may require the observer to be close to the ophthalmic device and hence close to the patient. With no extra optical components required this has the advantage of providing a low cost way of assessing cataract development.

An alternative way to observe the light reflected from the eye E is to place a further lens (not shown) in the observer's optical path 0. This would improve the resolution of the ophthalmic device and constrain the optical axis O. In addition it is possible to select a lens which would limit the depth of view to the patient's lens only. This would make the ophthalmic device easier to use initially but may constrain the use of the ophthalmic device in the case of patients having eyes without a large refractive error. In calculations undertaken the required refractive error (+/−5D) may be possible in the case of patients generally under the age of 50. (With age the eye losses its ability to focus over a wide range)

A further alternative for observing the light reflected from the eye E is to use a further lens (not shown) and then to display the image onto a small screen built into the ophthalmic device. The small screen may be, for example, a simple translucent plastic plate. This alternative, however, may limit the range of patient's eyes that can be viewed. This problem may be overcome by moving the instrument closer to the patient's eye E to improve focus. An alternative approach to improve focusing is to focus the objective lens (18, 46) until a sharp image is obtained. However, while this would improve observation it may also increase the cost of the ophthalmic device. Using the correct lenses, distances there between and screen distance, all of which should be determined by the overall size constraint of the ophthalmic device. optionally, the ophthalmic device may be designed to give an image of the cataractus lens only. This will allow the observer to be someway from the screen and therefore also from the patient. However, use of the screen may require a light source of high illumination.

Using the above designs of the ophthalmic device, their overall performance detecting and assessing cataract development was made using the Opticad software model. The "camcorder" design of ophthalmic device as shown in FIG. 21 was used for most of the work but results on a limited range of cataracts using the configuration of ophthalmic device shown in FIG. 20 yielded similar results. A range of rays from the LED source 40 were input into the Opticad model software and the reflectivity of the retina altered to assess the level of reflected light. All of these reflectivities proved to be adequate up to the thickest cataracts which had the optical effect of reducing the light to less than 5% of its normal level. At this point the high level of scattering also reduced the light reflected to the observer. Using the ophthalmic device of FIGS. 1, 10, 11 and 20, the observer would receive a reflected image straight back from the lens of the eye of the patient which would be obvious to an observer with minimal training. By moving the ophthalmic device around, the level of cataract may be assessed.

The level of scattering from the cataracts and the effect on the resulting reflected light is also simulated using the Opticad software model and the results are shown in FIGS. 22(a) to 22(d). As the scattering increases the reflected light becomes more diffuse.

Figure 22A:
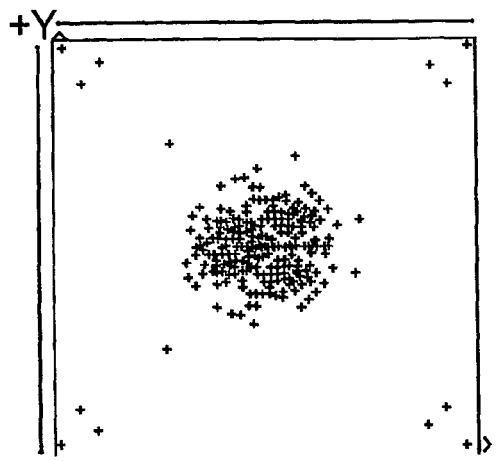
FIG. 22(a) is a plot showing the effect on the light reflected from the eye of a patient where no scattering is observed from cataracts.
Figure 22B:
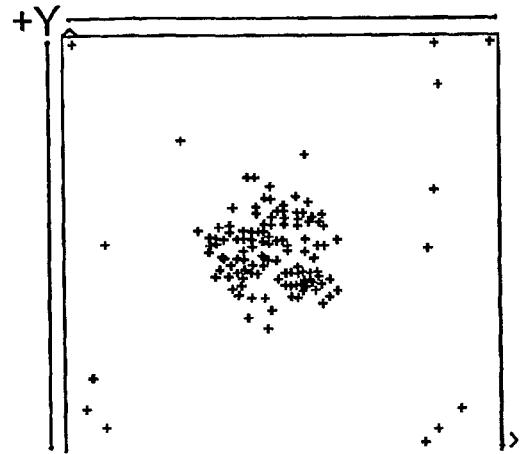
FIG. 22(b) is a plot showing the effect on the light reflected from the eye of a patient where 0.5 scattering is observed from cataracts.
Figure 22C:
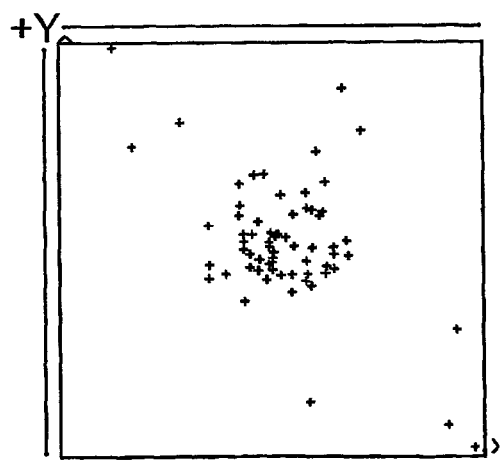
FIG. 22(c) is a plot showing the effect on the light reflected from the eye of a patient where 0.75 scattering is observed from cataracts.
Figure 22D:
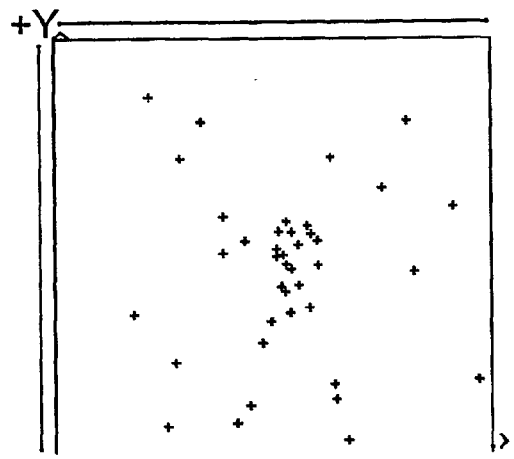
FIG. 22(d) is a plot showing the effect on the light reflected from the eye of a patient where 0.9 scattering is observed from cataracts.

As can be clearly seen, FIG. 22(a) shows scattering, and FIGS. 22(b) to 22(d) show 0.5, 0.75 and 0.9 scattering respectively.

The ophthalmic device either based on the "Lolly-pop" design as shown in FIGS. 1 to 12 and FIG. 20 or the "Camcorder" design as shown in FIGS. 13 to 15 and FIG. 21 will produce images of cataract that enable a trained but not highly skilled practitioner to determine the state of the patient's eye.

The reaction of the patient's eye to the light may also be considered. Without the use of mydriatic drugs the eye's natural response to the light will be to restrict the opening of the iris. This will tend to limit the observer's field of view of the patient's lens and developing cataract. Employing the Opticad software model an approximation was made from the light levels used what the retina would experience and it is judged that the iris would narrow to about 4 mm in diameter, though this may vary significantly from patient to patient, and the state of the cataract. With thicker cataracts the ophthalmic device may include a "boost" button to increase the light intensity and illumination level in order to produce a more clear image.

In terms of the overall design of the ophthalmic device the "Camcorder" design has certain advantages in the aesthetics of the design and the potential for the integration of the battery. The exact performance of this particular design of ophthalmic device will need to be evaluated further.

Figure 23:
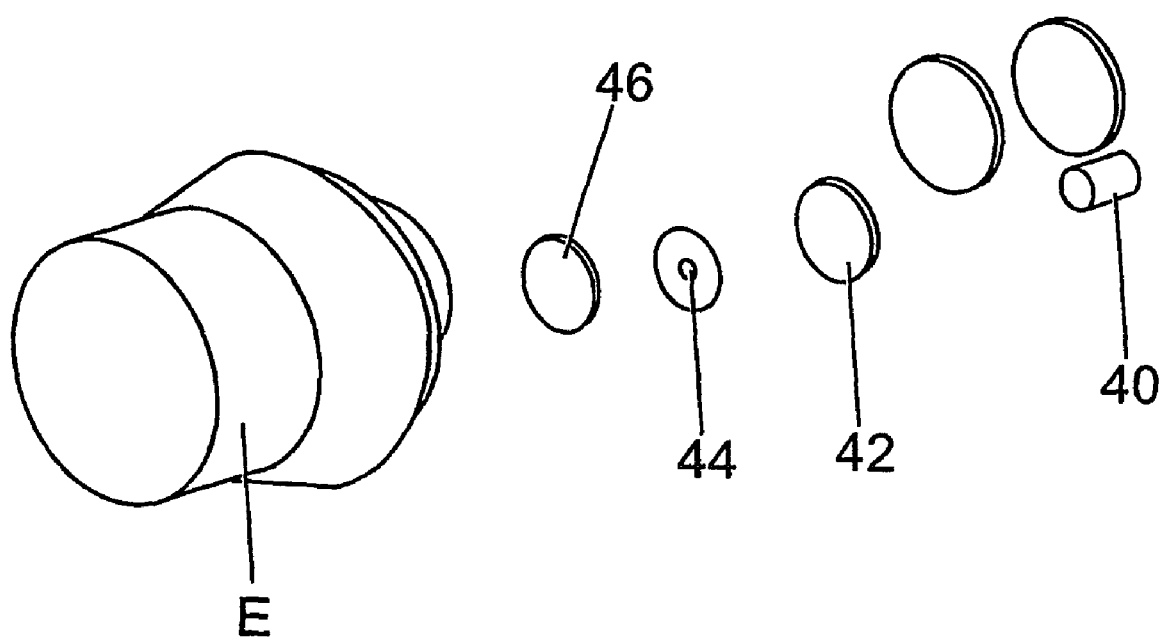
FIG. 23 is a view of a further embodiment of ophthalmic device without housing and positioned in relation to the patient's eye.

An ophthalmic device is shown in FIG. 23 based upon the "Camcorder design". This particular embodiment shows a lens and screen for the observation of the images without the housing 2.

The ophthalmic device shown in FIG. 23 is suitable for design into a clam shell housing with an integrated simple switch to operate the light source. The batteries could be replaceable or single use, with the option of "replacability". The ophthalmic device could be moulded as one item using a special polished tool, or standard components could be used.

The ophthalmic device may use standard COILS lenses. Smaller lenses are also suitable and these are of lower cost. The number of lenses used is not limited and the ophthalmic device may use 2, 3 or more lenses where appropriate.

Selection of a direct, lens or screen viewing is also an option with cost being added as the ophthalmic device becomes more complex. Suitable commercial screens and an allied lens could reduce the cost. The design of ophthalmic device may also need to determine the exact working distance required. Particular designs of ophthalmic device discussed above had a working distance of between 10-15 mm but this may be felt to be too close for some face shapes. Before designing the ophthalmic device it may be suitable to take these factors into account.

The advantages of the invention are many.

The ophthalmic device is a low-cost device which allows non-ophthalmologists accurately to identify cataract. The device is suitable for housing in a robust casing with fixed settings to allow a non ophthalmologist to determine the presence of visual acuities and in particular cataracts without recourse to mydriatic eye drops. The device suitably projects collimated or co-axial (or approximating co-axial) monochromatic light into the patient's eye directly or by way of a screen.

The low cost and simplicity of the ophthalmic device is of particular importance to Third World field work where screening workers of limited training often have the responsibility of providing cataract patients for high volume cataract units. This kind of responsibility is taken on by opticians and GP's in the UK and will grow in importance with the development of fast-track cataract services which allow direct referral of patients with cataract into a preoperative assessment clinic. The specificity of referrals appropriate to such a service will be directly dependent on the ability of non-ophthalmologists to identify and clinically grade the significance of cataracts.

It will be appreciated that the mirror 5 may be substituted with any suitable reflecting means, for example, a prismatic shaped reflector. The reflector may also have further optical devices, for example lenses, to promote illumination of the retina of the eye.

It will be appreciated that the mirror 4 may be a "one-way see-through" mirror, in which case the aperture 6 would not be required to define the light path 7.

It will also be appreciated that the light source may be separate or form an integral part of the ophthalmic device.

It will further be appreciated that the light source may form an integral part of the device 1 and may be of any suitable type, for example, a light emitting diode (LED).

It will be appreciated that the ophthalmic device may take the form of a number of shapes and is not limited to a cylindrical type shape as shown in the accompanying drawings. The ophthalmic device may also form part of a larger instrument and/or be removable and attached to another instrument.

The embodiments are not limited as hereinbefore described but may be varied in both construction and detail within the scope of the present invention.

The invention claimed is:

1. An ophthalmic device comprising:
   a housing having an illuminating through-hole and a viewing port disposed opposite the illuminating through-hole, and within the housing there being located:
   a light source arranged to project light out of the illuminating through-hole;
   a collimating lens located between the light source and the illuminating through-hole; and
   an objective lens located between the collimating lens and the illuminating through-hole;
   wherein the collimating lens and the objective lens are fixed within the housing to collimate the light projected out of the illuminating through-hole.

2. An ophthalmic device as claimed in claim 1, comprising a reflector located between the collimating lens and the objective lens and adapted to reflect light produced by the light source through the illuminating through-hole.

3. An ophthalmic device as claimed in claim 2, wherein the reflector comprises a generally planar reflecting surface oriented at an angle to maximize the reflection of light through the illuminating through-hole.

4. An ophthalmic device as claimed in claim 3, wherein the reflecting surface is oriented at an angle of approximately 45° to the light source.

5. An ophthalmic device as claimed in claim 2, wherein the reflector comprises a prismatic shaped reflector.

6. An ophthalmic device as claimed in claim 2, wherein the reflector comprises a one way see-through mirror.

7. An ophthalmic device as claimed in claim 2, wherein the reflector comprises a mirror.

8. An ophthalmic device as claimed in claim 2, wherein the reflector comprises a reflector through-hole, such that the illuminating through-hole, the reflector through-hole and the viewing port define a light path.

9. An ophthalmic device as claimed in claim 2, wherein the inner walls of the housing comprise a stop, intermediate one end of the housing and the reflector, to limit the depth of insertion of the light source into the housing.

10. An ophthalmic device as claimed in claim 2, wherein the reflector and the objective lens are formed as a unitary prismatic shaped reflector.

11. An ophthalmic device as claimed in claim 2, wherein the illuminating through-hole, the reflector and the viewing port are adapted to define a co-axial light path.

12. An ophthalmic device as claimed in claim 1, wherein the light source is an integral light source.

13. An ophthalmic device as claimed in claim 1, wherein the housing comprises a cylindrical tube.

14. An ophthalmic device as claimed in claim 1, wherein the housing comprises a reflector mounting.

15. An ophthalmic device as claimed in claim 14, wherein the reflector mounting comprises a pair of grooves on inner walls of the housing for receiving the reflector.

16. An ophthalmic device as claimed in claim 15, comprising a reflector secured within the grooves using a fixing substance.

17. An ophthalmic device as claimed in claim 1, wherein the light source is a monochromatic light source.

18. An ophthalmic device as claimed in claim 1, wherein the light source comprises a white light source.

19. An ophthalmic device as claimed in claim 1, wherein the light source comprises a pen torch receivable by an open end of the housing.

20. An ophthalmic device as claimed in claim 1, wherein the light source comprises a light emitting diode.

21. An ophthalmic device as claimed in claim 1, wherein an end of the housing remote from the light source is closed or sealed.

22. An ophthalmic device comprising a housing having an illuminating through-hole and a viewing port disposed opposite the illuminating through-hole, and within the housing there being located:
   a light source;
   a collimating lens located between the light source and the illuminating through-hole;
   an objective lens located between the collimating lens and the illuminating through-hole; and
   a reflector located between the collimating lens and the objective lens and adapted to reflect light produced by the light source through the illuminating through-hole;
   wherein the collimating lens and the objective lens are fixed within the housing to collimate the light projected out of the illuminating through-hole.

23. An ophthalmic device comprising:
   a housing having an illuminating through-hole and a viewing port disposed opposite the illuminating through-hole;
   a light source;
   an optical device within the housing having a collimating lens between the light source and the illuminating through-hole and an objective lens between the collimating lens and the illuminating through-hole, and arranged to receive light from the light source, collimate the light, and direct the collimated light to the illuminating through-hole.

24. The ophthalmic device according to claim 23 wherein the collimating lens and the objective lens are fixed within the housing.

25. The ophthalmic device according to claim 23 wherein the light follows a light path from the light source to the illuminating through-hole and the optical device comprises a prism positioned along the light path.

26. The ophthalmic device according to claim 23 wherein the light follows a light path from the light source to the illuminating through-hole and the optical device comprises a reflector positioned along the light path.

* * * * *